(12) United States Patent
McDermott et al.

(10) Patent No.: US 6,469,780 B1
(45) Date of Patent: Oct. 22, 2002

(54) APPARATUS AND METHOD FOR DETECTING PARTICLES IN REACTIVE AND TOXIC GASES

(75) Inventors: Wayne Thomas McDermott, Fogelsville; Richard Carl Ockovic, Northampton, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/217,113

(22) Filed: Dec. 21, 1998

(51) Int. Cl.[7] ................................................. G01N 1/00
(52) U.S. Cl. ........................ 356/37; 356/335; 356/336
(58) Field of Search .......................... 356/37, 335, 336, 356/342

(56) References Cited

U.S. PATENT DOCUMENTS

| | | | |
|---|---|---|---|
| 3,632,210 A | 1/1972 | Rich | 356/37 |
| 3,806,248 A | 4/1974 | Sinclair | 356/37 |
| 4,293,217 A | 10/1981 | Bird, Jr. et al. | 356/37 |
| 4,790,650 A | 12/1988 | Keady | 356/37 |
| 5,026,155 A | 6/1991 | Ockovic et al. | 356/37 |
| 5,231,865 A | 8/1993 | McDermott et al. | 73/28.04 |
| 5,872,622 A | * 2/1999 | Schildmeyer et al. | 356/37 |
| 5,903,338 A | * 5/1999 | Mavliev | 356/37 |

OTHER PUBLICATIONS

M. R. Stolzenburg, particularly Chapter 5, titled An UltrafineAerosol Condensation Nucleus Counter. 1988.

"A Condensation Nucleus Counter Design for Ultrafine Particle Detection Above 3 nm Diameter" by P. B. Keady, V. L. Denier, G. J. Sero, M. R. Stolzenburg and P. H. McMurry. 1989.

M. R. Stolzenburg and P. H. McMurry, entitled "Counting Efficiency of an Ultrafine Aerosol Condensation Nucleus Counter: Theory and Experiment". 1986.

A. E. Holmer, M. L. Malczewski, J. Blesener and G. Schürmann entitled "Design and Calibration of a Condensation Nucleus Counter Suitable for Use in Hydrogen Service". 1993.

H. T. Sommer, J. R. C. Futrell, L. R. Dominguez–Sommer and D. D. Christman entitled "Condensation Nucleus Counter Evaluation for Hazardous Semiconductor Process Gases". Oct. 28–30, 1992.

B. Y. H. Liu and Y. H. Pui entitled "A Submicron Aerosol Standard and the Primary, Absolute Calibration of the Condensation Nuclei Counter". 1974.

Model 7651; Reactive Gas Condensation Particle Counter. Particle Measuring Systems, Inc. 1994.

Model CNC–1107; Condensation Nucleus Counter for Reactive Gases. Met One. 11/92.

* cited by examiner

*Primary Examiner*—Frank G. Font
*Assistant Examiner*—Ray M. Punnoose
(74) *Attorney, Agent, or Firm*—Geoffrey L. Chase

(57) ABSTRACT

An apparatus and a method are disclosed for detecting particles in a particle-containing gas at a pressure greater than about 0 psig. The apparatus includes a gas distribution line containing a pressurized gas having a pressure greater than about 0 psig and a condensation nucleus counter in fluid communication with the pressurized gas in the gas distribution line. The condensation nucleus counter is adapted to receive a stream of the pressurized gas at a pressure substantially equal to the pressure of the pressurized gas in the gas distribution line. The condensation nucleus counter is constructed of materials resistant to corrosion and to reaction with the pressurized gas, which may be one or more reactive or toxic gases, such as those used in microchip processing, or an inert gas.

19 Claims, 4 Drawing Sheets

APPARATUS AND METHOD FOR DETECTING PARTICLES IN REACTIVE AND TOXIC GASES

CROSS-REFERENCE TO RELATED APPLICATIONS

Not Applicable.

STATEMENT REGARDING FEDERALLY SPONSORED RESEARCH FOR DEVELOPMENT

Not Applicable.

BACKGROUND OF THE INVENTION

The present invention relates to the field of particle counting in gases, particularly reactive, corrosive gases for the electronics fabrication industry.

Minute amounts of contamination can adversely affect the microchip fabrication process in the electronics industry. Contamination in the form of particles causes short circuits, open circuits, and other defects. These defects can cause finished micro-electronic circuits to fail. Such failures are responsible for significant yield reductions in the microelectronics industry. Yield reductions caused by microcontamination substantially increase processing costs.

Micro-electronic circuits require many processing steps. Processing is performed using extremely clean gases. However, the amount of contamination needed to produce fatal defects in micro-circuits is extremely small. For example, an individual particle as small as 0.02 micrometer in diameter can result in a fatal defect in a modern microcircuit. Micro-contamination may occur at any time during the many steps needed to complete a circuit. Therefore, tight control of cleanliness in the processing gas is required.

Modern filters are able to remove particulate contaminants in process gases with an extremely high efficiency. However, the complete assurance of contamination control also requires verification of gas cleanliness. An accurate technique for detecting microscopic particles in filtered gases must be available. This technique must be capable of detecting microscopic contaminant particles as small as 0.02 micrometer in reactive or toxic gases used in microchip processing, including but not limited to the following gases: $SiCl_4$, $PH_3$, $B_2H_6$, $AsH_3$, $SiF_4$, $Si_2H_6$, $NH_3$, $BCl_3$, $BF_3$, $Cl_2$, $H_2$, $HBr$, $HCl$, $HF$, $NF_3$, $N_2O$, $O_2$, $SiH_4$ and $WF_6$, as well as inert gases, including, but not limited to such gases as $N_2$, $Ar$, $He$, $CF_4$, $CHF_3$, $C_2F_6$ and $SF_6$.

Ideally, the technique should perform the particle measurement at a pressure equal to the process gas system line pressure (about 60 psig). By performing the measurement at the gas line pressure, the sample gas would not need to be reduced in pressure before entering the measuring instrument. That is, the instrument could be connected directly to the gas line without intermediate pressure reducing devices. Measurement at gas line pressure would provide an advantage in particle measurement, since the process of pressure reduction in some gases can produce adverse effects such as particle shear-off or nucleation of impurities in the pressure reduction device. Such objects produced by shear-off or nucleation would be falsely interpreted by the downstream particle counting instrument as gas line contaminant particles.

Also, many pressure reduction devices require venting a portion of hazardous and expensive gases before the remaining sample can enter the instrument. Such venting is costly, environmentally damaging, and may require increased flow capacities through vent system emission control devices.

Finally, condensation of the process gas into liquid droplets may occur during the process of pressure reduction, especially when sampling high boiling point and easily condensed gases such as HF, $WF_6$ and $BCl_3$. Such condensation droplets also would be falsely interpreted by the downstream particle counting instrument as gas line contaminant particles.

It is therefore advantageous to develop a sampling technique that can measure contaminant particles as small as 0.02 micrometer in toxic or reactive microchip processing gases without the need for intermediate gas pressure reduction.

Previous attempts to obtain continuous counting of contaminant particles in reactive or toxic process gases, as well as inert gases, have included laser particle spectrometers or laser particle monitors. These instruments determine the equivalent optical diameters of contaminant particles through a process of light scattering from individual particles. The number of light pulses scattered is equal to the number of particles passing through the optical sensing volume of the instrument. Such instruments have been developed for use with reactive or toxic gases, and for pressurized sample gases. Modern laser particle counters typically function with low background noise for particles larger than 0.1 micrometer, but are noise limited in lower size detection capability because of light scattering from sub-range particles and gas molecules. Consequently, such instruments cannot detect contaminant particles smaller than 0.1 micrometer.

Previous attempts to obtain low noise particle detection below 0.1 micrometer have included condensation nucleus counters (CNCs). These instruments use continuous conductive cooling, continuous cooling through dilution, or cooling through expansion to create a supersaturated aerosol mixture. Various substances have been used as a saturating medium, including water, alcohol (e.g., butanol) and perfluorinated organic compounds, such as perfluorodimethyldecalin. The fine particles act as nucleation sites for vapor condensation and subsequent droplet growth. Droplets grow to sufficient size to permit detection by conventional light scattering or light absorption techniques with negligible accompanying noise.

Such a CNC has been described in U.S. Pat. No. 4,790,650 wherein a device admits a gaseous flow into a saturator zone and then takes a portion of the flow through a chilled region to condense a working fluid on entrained particles to enlarge the diameter of the particle to facilitate counting by downstream means, such as an optical particle detection device.

Additional descriptions of CNCs are found in the dissertation by M. R. Stolzenburg, particularly Chapter 5, titled "An Ultrafine Aerosol Condensation Nucleus Counter", and in an article titled "A Condensation Nucleus Counter Design for Ultrafine Particle Detection Above 3 nm Diameter" by P. B. Keady, V. L. Denier, G. J. Sero, M. R. Stolzenburg and P. H. McMurry.

U.S. Pat. No. 4,293,217 discloses a continuous flow CNC and process for detecting small contaminants in gas streams. Additional patents pertaining to CNC's include U.S. Pat. Nos. 3,806,248 and 3,632,210.

The theory and operation of one type of CNC is set forth in an article by M. R. Stolzenburg and P. H. McMurry, entitled "Counting Efficiency of an Ultrafine Aerosol Condensation Nucleus Counter: Theory and Experiment".

The above CNCs were developed for use only with inert sample gases. A CNC designed for use in $H_2$ and $O_2$, as well as inert gases such as $N_2$ and He, was described in an article by A. E. Holmer, M. L. Malczewski, J. Blesener and G. Schurmann entitled "Design and Calibration of a Condensation Nucleus Counter Suitable for Use in Hydrogen Service".

A CNC designed for use in $H_2$ and $O_2$, as well as inert gases such as $N_2$, was described in an article by H. T. Sommer, J. R. C. Futrell, L. R. Dominguez-Sommer and D. D. Christman entitled "Condensation Nucleus Counter Evaluation for Hazardous Semiconductor Process Gases".

An alternative method for measuring particles in reactive gases is disclosed in U.S. Pat. No. 5,231,865. This patent discloses a diffusion gas diluter device and a method wherein a particle-containing reactive gas, such as $H_2$ or $O_2$, is diluted with an inert diluent gas to diminish the reactive characteristics of the particle-containing gas without disturbing the particle concentration of the gas, thus allowing it to be accurately and safely measured for its particle content using a conventional inert gas CNC.

The measurement techniques in the above references are capable in some cases of detecting particles in $H_2$ and $O_2$, and can in some cases detect particles as small as 0.003 micrometer. However, those techniques do not detect particles as gas pressures above 0 psig in toxic or other reactive gases, such as $SiCl_4$, $PH_3$, $B_2H_6$, $AsH_3$, $SiF_4$, $Si_2H_6$, $NH_3$, $BCl_3$, $BF_3$, $Cl_2$, Hbr, Chl, HF, $NF_3$, $N_2O$, $SiH_4$, and $WF_6$.

Several prior CNCs have been developed for use with an oxidizing gas ($O_2$) or a flammable gas ($H_2$). However, many prior CNCs and their contained working fluids were constructed from materials that are not resistant to reaction with oxidizing or flammable gases. Most prior CNCs were developed for use with air or inert gases. These CNCs were constructed from materials that typically are not resistant to chemical attack from corrosive gases.

The prior CNCs were not constructed to contain gas pressures greater than 0 psig, or to prevent possible leakage of reactive or toxic gases under pressure. Therefore, the prior CNCs require upstream pressure reduction when sampling from pressurized gas sources.

It is desired to have an apparatus and a method for counting and measuring particles substantially smaller than 0.1 micrometer in gases at elevated pressures (i.e., greater than 0 psig), especially toxic and/or reactive gases, including but not limited to such gases used in microchip processing.

It is further desired to have such an apparatus and method which can perform such measurements and counting of particles at pressures substantially equal to process gas system line pressures, typically about 60 psig (i.e., without the need for upstream or intermediate pressure reducing devices).

It is still further desired to have such an apparatus which is constructed from materials that are resistant to corrosion and to reaction with oxidizing or flammable gases, and which can contain elevated pressures (e.g., about 60 psig) and prevent leakage of reactive and/or toxic gases under pressure.

BRIEF SUMMARY OF THE INVENTION

The present invention is an apparatus and a method for detecting particles in a particle-containing gas at a pressure greater than about 0 psig. The invention can detect sub-0.1 micrometer contaminant particles in pressurized reactive or toxic gases, including but not limited to $SiCl_4$, $PH_3$, $B_2H_6$, $AsH_3$, $SiF_4$, $Si_2H_6$, $NH_3$, $BCl_3$, $BF_3$, $Cl_2$, $H_2$, HBr, HCl, HF, $NF_3$, $N_2O$, $O_2$, $SiH_4$, $WF_6$, and mixtures thereof, as well as inert gases, including but not limited to $N_2$, Ar, He, $CF_4$, $CHF_3$, $C_2F_6$, and $SF_6$, and mixtures thereof.

In a preferred embodiment, the apparatus includes a gas distribution line containing a pressurized gas having a pressure greater than about 0 psig and a condensation nucleus counter in fluid communication with the pressurized gas in the gas distribution line. The condensation nucleus counter is adapted to receive a stream of the pressurized gas at a pressure substantially equal to the pressure of the pressurized gas in the gas distribution line.

In another embodiment, the apparatus also includes means for determining the number of at least one particle in the pressurized gas. In yet another embodiment, the apparatus includes means for tabulating the number of the at least one particle. For example, the means for tabulating may be a computer.

In the preferred embodiment, the condensation nucleus counter includes the following: (a) a reservoir block; (b) an inlet tube adapted to receive the stream of the pressurized gas and to deliver said stream into the reservoir block; (c) a saturator disposed inside the reservoir block, wherein the saturator is heated by a heater mounted in thermal contact with the reservoir block; (d) a working fluid disposed inside the saturator; (e) a sintered metal wick partially submerged in the working fluid; (f) a condenser adapted to receive a stream of the pressurized gas from the saturator; (g) an aerodynamic focusing nozzle adapted to receive the stream of the pressurized gas stream containing droplets; (h) an optical detection chamber having a droplet sensing device to count and identify the droplets in the pressurized gas stream containing droplets; (i) and an outlet tube adapted to vent the pressurized gas stream containing droplets from the optical detection chamber.

The condensation nucleus counter is constructed of materials resistant to corrosion and to reaction with any of several pressurized gases, including but not limited to: $SiCl_4$, $PH_3$, $B_2H_6$, $AsH_3$, $SiF_4$, $Si_2H_6$, $NH_3$, $BCl_3$, $BF_3$, $Cl_2$, $H_2$, HBr, HCl, HF, $NF_3$, $N_2O$, $O_2$, $SiH_4$, $WF_6$, $N_2$, Ar, He, $CF_4$, $CHF_3$, $C_2F_6$, and $SF_6$, and mixtures thereof.

Another aspect of the invention is a method of detecting particles in a particle-containing gas at a pressure greater than about 0 psig. The method includes multiple steps as follows: (a) providing a gas distribution line containing a pressurized gas at a pressure greater than about 0 psig; (b) providing a condensation nucleus counter in fluid communication with the pressurized gas in the distribution line, wherein the condensation nucleus counter is adapted to receive a stream of pressurized gas at pressures substantially equal to the pressure of the gas in the pressurized gas distribution line; and (c) introducing a stream of the pressurized gas into the condensation nucleus counter at a pressure substantially equal to the pressure of the pressurized gas in the gas distribution line.

In an alternate embodiment, the method includes the additional step of determining the number of at least one particle in the pressurized gas introduced into the condensation nucleus counter. In yet another embodiment, the method includes the additional step of tabulating the number of the at least one particle. For example, the tabulating step may be performed by a computer.

The step of determining the number of at least one particle in the pressurized gas comprises the following sub-steps: (a) passing a particle-containing gas mixed with a fluid vapor into a condensation zone; (b) condensing the working fluid vapor on at least one particle in the particle-containing gas having a minimum size corresponding to a minimum temperature of a condensing zone to form at least one droplet; and (c) detecting the droplets and counting the number of droplets by appropriate sensing and tabulation.

The working fluid may be perfluorotrimethyllcyclohexane. However, other fluids may be used, including but not limited to non-reactive fluids, such as Multfluor® perfluorinated hydrocarbons, available from Air Products and Chemicals, Inc. of Allentown, Pa. (Multifluor® is a registered trademark of Air Products and Chemicals, Inc.).

Using the methods according to the present invention, the particles in a particle-containing pressurized gas can be detected at an at least approximately 50% counting efficiency. A typical pressure of the gas in such a method is about 60 psig. The methods may be used for any of several pressurized gases, including but not limited to: $SiCl_4$, $PH_3$, $B_2H_6$, $AsH_3$, $SiF_4$, $Si_2H_6$, $NH_3$, $BCl_3$, $BF_3$, $Cl_2$, $H_2$, HBr, HCl, HF, $NF_3$, $N_2O$, $O_2$, $SiH_4$, $WF_6$, $N_2$, Ar, He, $CF_4$, $CHF_3$, $C_2F_6$, and $SF_6$, and mixtures thereof.

Another aspect of the invention is an improved gas distribution system containing a pressurized gas having a pressure greater than about 0 psig including a condensation nucleus counter in fluid communication with the pressurized gas distribution system. The condensation nucleus counter is adapted to receive a stream of the pressurized gas at a pressure substantially equal to the pressure of the gas in the gas distribution system.

BRIEF DESCRIPTION OF THE DRAWINGS

The invention will now be described by way of example with reference to the accompanying drawings, in which.

DETAILED DESCRIPTION OF THE INVENTION

The present invention is an apparatus and method to detect and measure particles substantially smaller than 0.1 micrometer in toxic or reactive gases at elevated pressures (i.e., greater than 0 psig). In particular, the invention is an apparatus and method for detecting sub-0.1 micrometer particles in toxic or reactive gases at gas line pressures of about 60 psig using a condensation nucleus counter constructed of materials resistant to corrosion and to reaction with the pressurized toxic or reactive gases. The present invention is useful in particle detection in gas distribution systems, including but not limited to systems for delivering gases from a point of storage to a point of utilization. Such systems typically have storage containers, control valves, manifolds, flow controllers, distribution lines and monitoring equipment.

Figure 1:
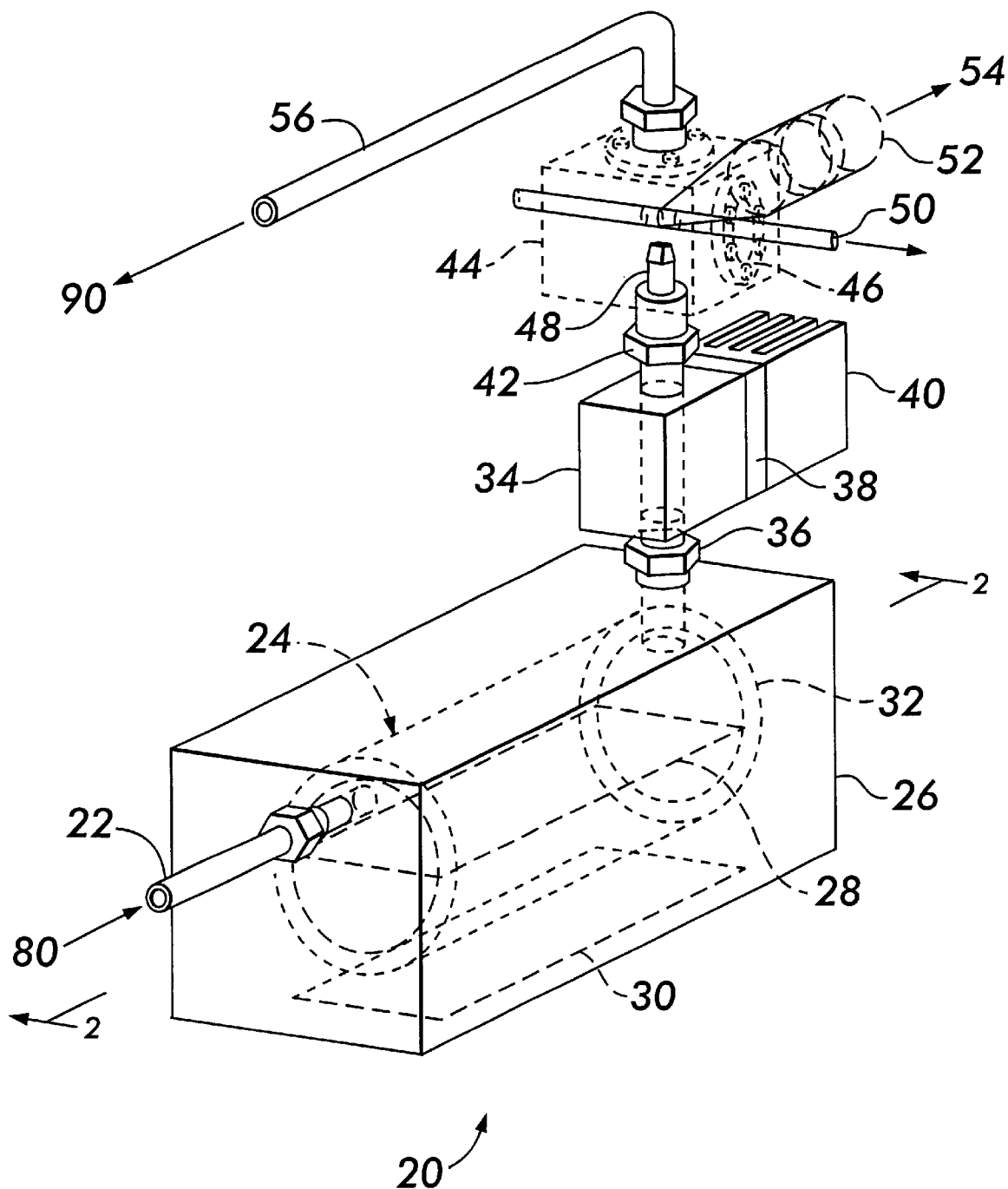
FIG. 1 is a perspective view of a condensation nucleus counter according to the present invention.
Figure 2:
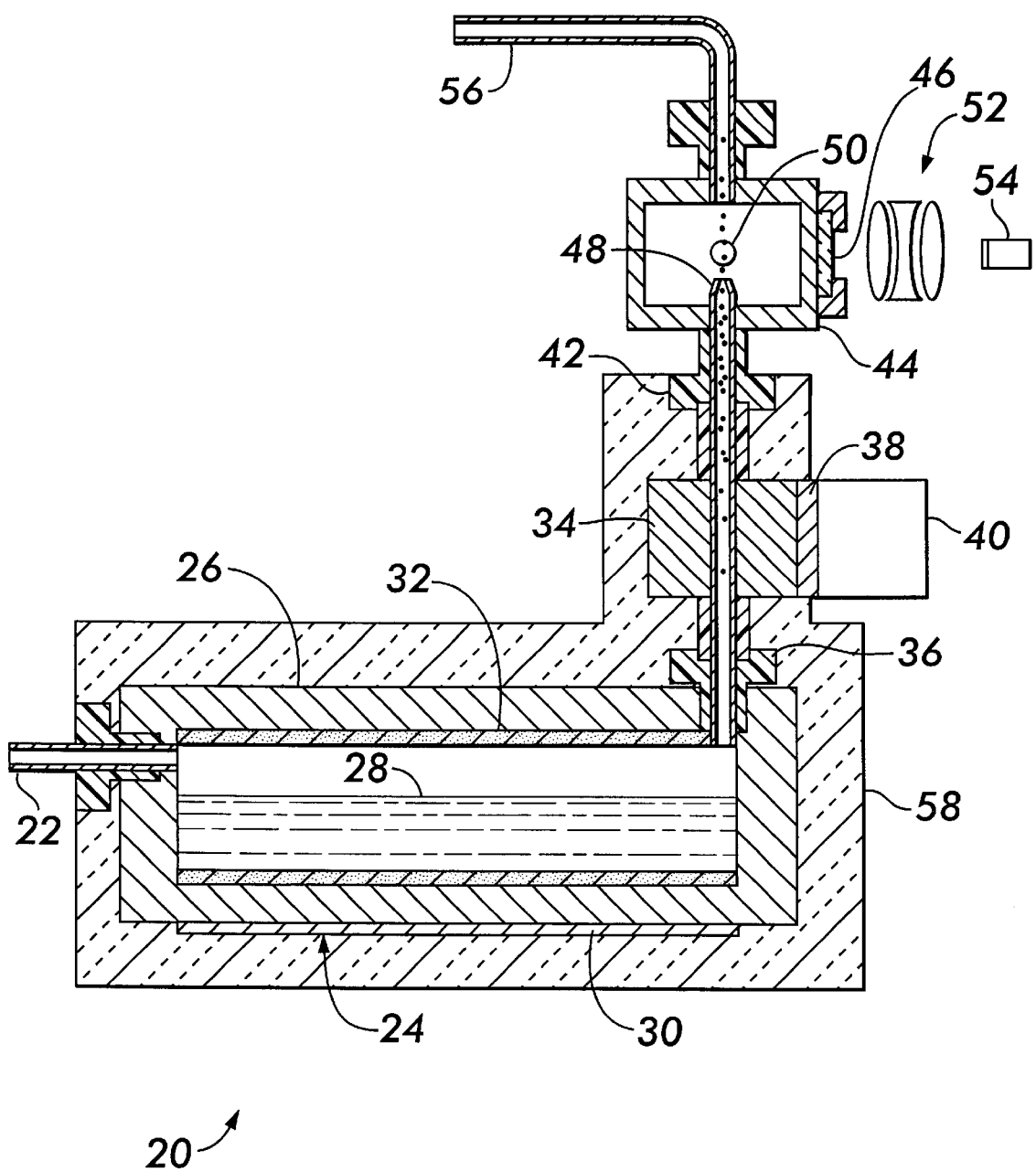
FIG. 2 is a cross-sectional side view taken along lines 2—2 of the condensation nucleus counter shown in FIG. 1 with the addition of thermal insulation and a photo detector.
Figure 3A:
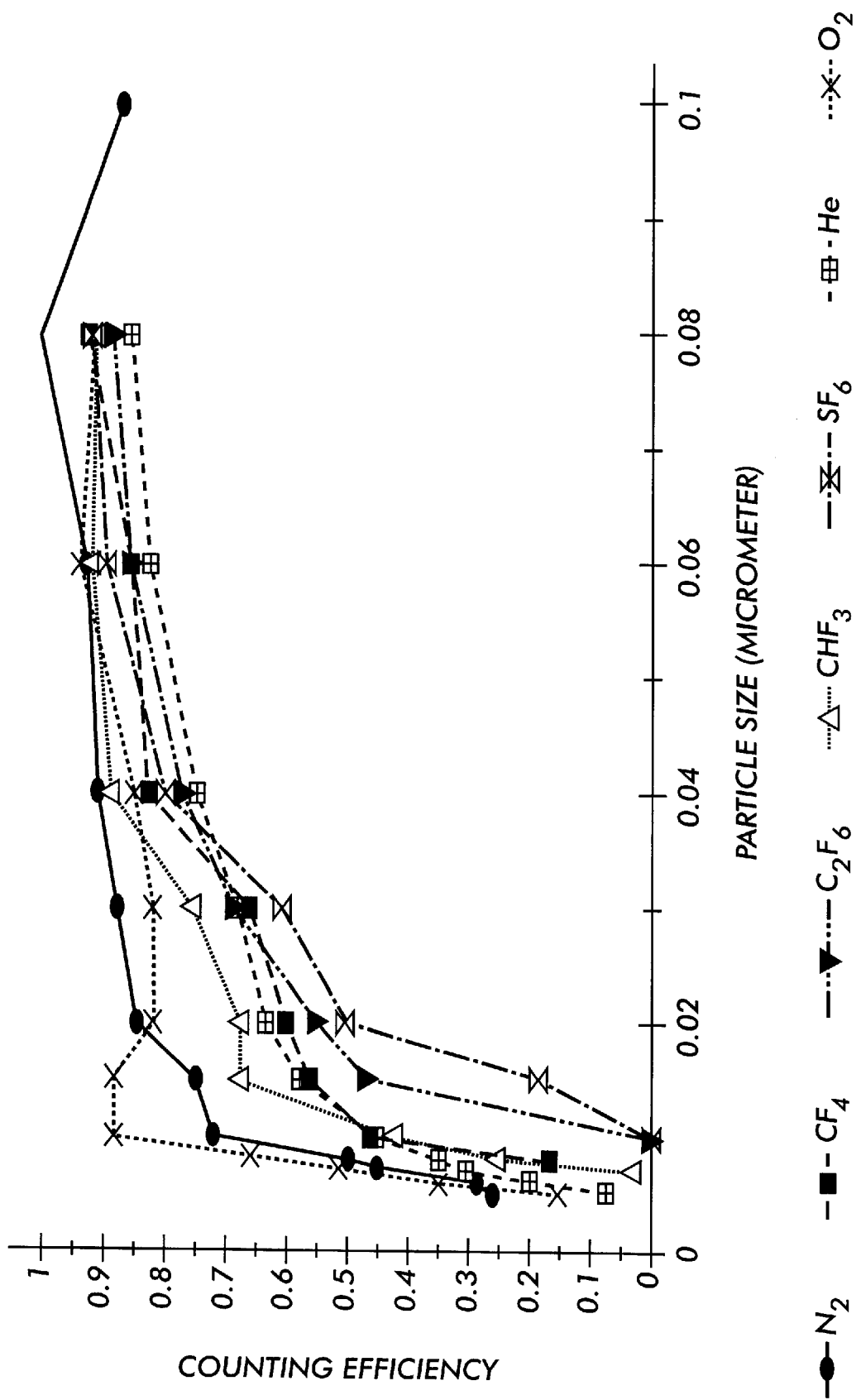
FIG. 3A is a graph illustrating the counting efficiency of the condensation nucleus counter according to the present invention for seven different gases.
Figure 3B:
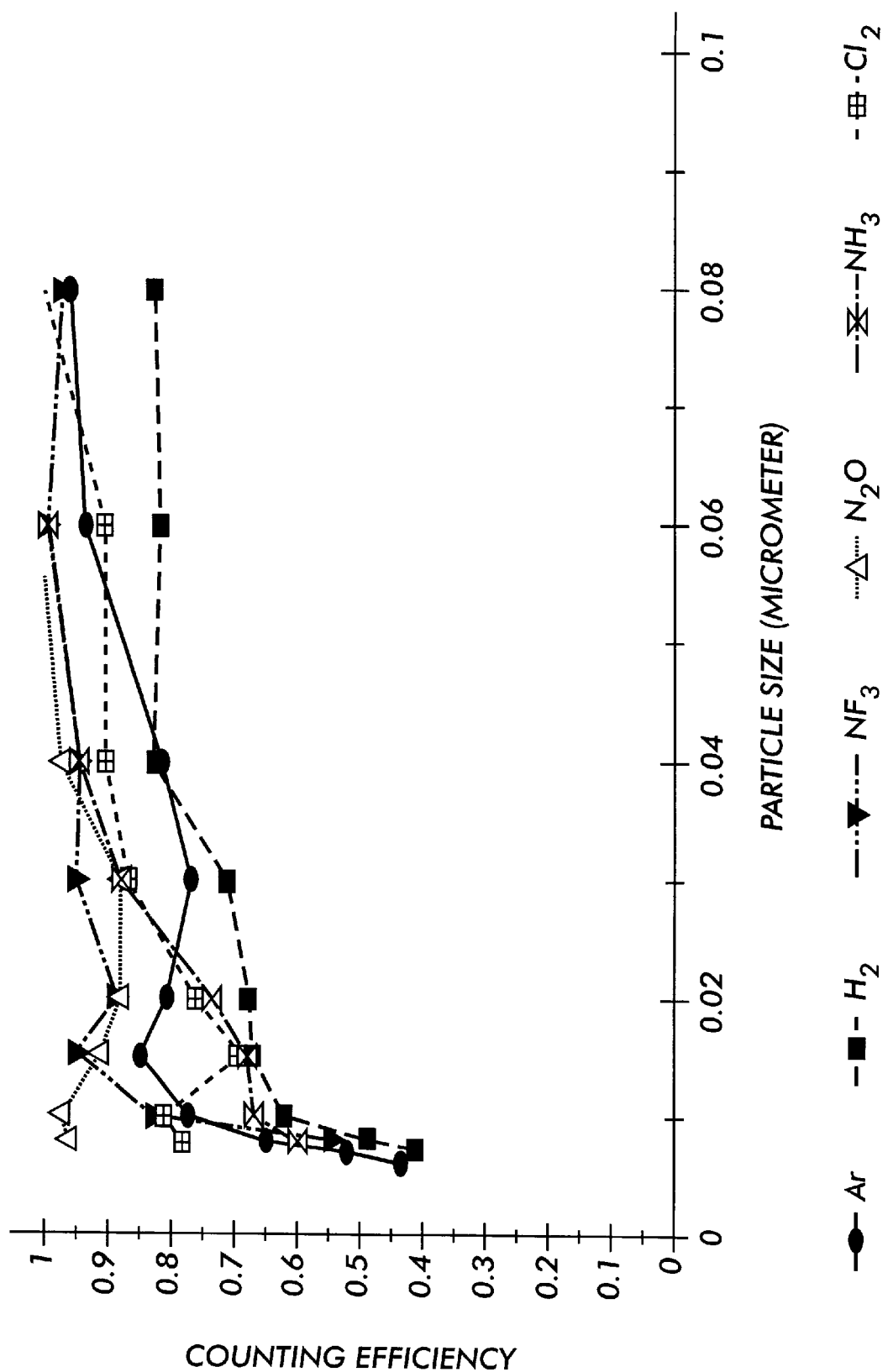
FIG. 3B is a graph illustrating the counting efficiency of the condensation nucleus counter according to the present invention for six other gases.

Referring to FIGS. 1 and 2, the present invention includes a gas distribution line (not shown) containing a pressurized gas having a pressure greater than about 0 psig and a condensation nucleus counter 20 in fluid communication with the pressurized gas in the gas distribution line. As indicated in FIG. 1, the condensation nucleus counter receives a stream 80 of the pressurized gas from the gas distribution line. The stream is at a pressure substantially equal to the pressure of the pressurized gas in the gas distribution line. The condensation nucleus counter (CNC) is designed to measure particles substantially smaller than 0.1 micrometer in toxic or reactive gases at elevated pressures.

Referring to FIGS. 1 and 2, the main components of the CNC 20 in the preferred embodiment are:

gas inlet tube 22 saturator 24 (composite of: 26, 28, 30 & 32)

reservoir block 26 working fluid 28 electrical resistance heater pad 30 tubular sintered metal wick 32 condenser 34

Teflon connector 36 between the saturator 24 and the condenser 34 thermo-electric cooler 38 for the condenser 34 condenser/heat fins 40

Teflon connector 42 between the condenser 34 and the optical detector chamber 44 optical detector chamber 44 with quartz windows 46 aerodynamic focusing nozzle 48 laser 50, collection optics 52, and photo-detector 54 (not shown in FIG. 1)

gas outlet tube 56 thermal insulation 58 (not shown in FIG. 1) surrounding the saturator 24, condenser 34, and teflon connectors 36, 42.

The gas inlet tube 22, saturator 24, sintered metal wick 32, condenser 34, aerodynamic focusing nozzle 48, optical detector chamber 44, and gas outlet tube 56 are constructed from Monel alloy, Inconel alloy, or other suitable thermally conducting and corrosion resistant materials, and are properly sized to withstand elevated pressures such as, for example, about 60 psig.

The optical detector chamber windows 46 are constructed from quartz or other suitable corrosion resistant and optically transparent material, and are sized to withstand elevated pressures such as, for example, about 60 psig.

The connectors (36, 42) between the saturator 24 and the condenser 34, and between the condenser and the optical detector chamber 44 are constructed from Teflon plastic, Delrin plastic, or other suitable thermally insulating and corrosion resistant material. The thermal insulation provided by these connectors permits the saturator, condenser and optical detector chamber to be thermally isolated from each other and maintained at different operating temperatures.

The working fluid 28 can consist of any one of the family of non-reactive inert liquids, including but not limited to perfluorotrimentylcyclohexane and other perfluorinated hydrocarbon compounds. Such fluids include Multifluor® fluids, available from Air Products and Chemicals, Inc. of Allentown, Pa. (Multifluor® us a registered trademark of Air Products and Chemicals, Inc.).

The CNC 20 counts particles in a particle-containing gas using condensation nucleus counting, comprising the following steps: passing a particle-containing gas mixed with a working fluid vapor into a condensation zone defined by condenser 34; condensing working fluid vapor on that portion of the particles of a minimum size corresponding to a minimum temperature of the condensing zone to form droplets; and detecting the droplets and counting the number of droplets by appropriate sensing and tabulation, such as the optical detector chamber 44, photodetector 54 and its associated hardware and a computer capable of tabulation, as well known in the art.

The saturated 24 and working fluid 28 are maintained at a typical elevated temperature of about 85° F. using an electrical resistance heater 30 mounted in thermal contact with the external surface of the reservoir block 26. A saturator-mounted temperature sensor (not shown) and power control circuit (not shown) permit the saturator and working fluid to be held at a constant, selected temperature. A particle-containing sample gas stream 80 from the pressurized gas distribution line (not shown) is warmed and saturated in working fluid vapor as the sample gas passes through the saturator at a typical flow rate of about 150 standard cubic centimeters per minute. The tubular sintered metal wick 32 is partially submerged in the working fluid and provides a wetted surface to surround the sample gas as it flows through the saturator, thus enhancing the saturation process.

The condenser 34 is maintained at a typical reduced temperature of about 35° F. using a thermoelectric cooler 38 mounted in thermal contact with the condenser. In the preferred embodiment, the condenser has an inside diameter of about 0.189 inch and a length of about 2.16 inches. Persons skilled in the art will recognize, however, that condensers of other sizes may be used.

A condenser-mounted temperature sensor (not shown) and power control circuit (not shown) permit the condenser to be held at a constant, selected temperature. Heat is removed from the condenser by the thermo-electric cooler and released into the externally mounted and convectively cooled heat fins 40. The particle-containing and saturated gas becomes super-saturated in working fluid vapor as it passes through the cooled condenser. The particles act as nucleation sites for droplets which form from condensing working fluid on the particles. The droplets grow to a size sufficient to be easily detected using light scattering.

The gas flow containing the droplets then passes through the aerodynamic focusing nozzle 48 and into the optical detection chamber 44. The focusing nozzle directs all the droplets into the path of the light source from laser 50. As the droplets pass through the light source they scatter light into the collection optics 52 leading to a photo-detector 54 (not shown in FIG. 1). The photo-detector provides an electrical reading that is transmitted to a tabulation device (not shown), such as a computer or data processor. The resulting gas is then removed through gas outlet tube 56 to a flare, scrubber, or other emission control device 90 (not shown). A flow control device (not shown) on gas outlet tube 56 or gas inlet tube 22 may be used to regulate the gas flow to and from the CNC 20.

The droplet sensing device typically consists of a light source, focusing optics, narrow slit (collectively 50), viewing volume (stream discharge of 48), collecting optics 52 and photo-detector 54. Individual droplet detection is typically accomplished through a process of light scattering. A single pulse of scattered light is generated for each droplet traveling through the viewing volume. The photo-detector converts the light pulses into electrical pulses which are typically counted in a triggering circuit. Tabulated droplet counts can be converted directly to particle concentration in the gas using the known gas flow rate.

The combination of the above elements provides a CNC 20 that can detect particles as small as 0.02 micrometer with high efficiency. This performance was demonstrated by introducing particles of a known narrow size range into the CNC and measuring the efficiency with which the CNC counted the particles. The measurement was repeated over a range of particle sizes to obtain the characteristic response curve of the CNC, known as the counting efficiency curve. The counting efficiency is approximately 100% (1.0) for large, particles, i.e., particles having diameters well above the minimum detectable size. However, the counting efficiency falls to zero at the minimum detectable particle size.

Particles were produced by vaporizing sodium chloride in heated nitrogen at approximately 900° C., and then quickly diluting the mixture with cool filtered nitrogen. The rapid dilution produced fine sodium chloride particles having a continuous distribution of sizes ranging from 0.004 micrometer to 0.2 micrometer. The resulting aerosol was reduced to a narrow size range by flowing it through an electrostatic classifier, or differential mobility analyzer. The differential mobility analyzer rejects all particles except those near a selected size. The aerosol is charge neutralized by exposing it to radiation from a Krypton-85 source. Nearly all of the neutralized particles contain either a zero or a unit charge. The neutralized aerosol is then flowed into a differential mobility analyzer. The mobility analyzer is used to extract particles having a selected electrical mobility. The electrical mobility $Z_p$ (cm$^2$/volt-sec) of a singly charged particle is related to the particle size as follows:

$$Z_p = \frac{eC \times 10^7}{3\pi\mu D_p}$$

where $D_p$ is the particle diameter, $e=1.6\times10^{-19}$ coulombs, C is the non-dimensional slip correction factor for the particles and $\mu$ (poise) is the gas viscosity. The differential mobility analyzer flows the aerosol and a filtered sheath gas through two concentric circular electrodes having radii $r_1$ and $r_2$ and length L (cm). A dc voltage V is applied to the electrodes to generate an electric field perpendicular to the flow direction. The trajectories of the charged particles are altered by the electric field. The paths followed by the diverted particles are determined by their specific electrical mobility. Particles following a selected path are removed through a slit at the end of the electrodes. All other particles are vented or deposited on the electrodes. The electrical mobility of the particles is given by:

$$Z_p = \frac{\left[q_t - \frac{1}{2}(q_s + q_a)\right]\ln(r_2/r_1)}{2\pi VL}$$

where $q_t$ is the total flow rate through the analyzer, $q_s$ is the slit flow rate and $q_a$ is the inlet aerosol flow rate (cm$^3$/sec). The resulting narrow band sodium chloride aerosol is then split into two streams. One stream flowed to the CNC, while the other stream is directed into an aerosol electrometer. Measurements of particle concentration obtained from the CNC are then directly compared to those obtained from the electrometer in order to determine the counting efficiency of the CNC. The particle size of the narrow band aerosol is then varied by adjusting the voltage of the differential mobility analyzer in order to obtain the counting efficiency curve of the CNC. The above test procedure was fully described in an article by B. Y. H. Liu and Y. H. Pui entitled "A Submicron Aerosol Standard and the Primary, Absolute Calibration of the Condensation Nuclei Counter", Journal of Colloidal and Interface Science, Vol. 47, No. 1, Apr. 1974, pp. 155–171.

The CNC 20 according to the present invention differs from previous attempts to obtain continuous counting of contaminant particles substantially smaller than 0.1 micrometer in process gases in that it is completely constructed from materials resistant to corrosion as well as reaction with oxidizing or flammable gases. Also, the CNC is designed to contain elevated pressures such as, for example, about 60 psig and to prevent leakage of reactive or toxic gases under pressure. Since the CNC can contain sample gases at full gas line pressure, contaminant particles can be detected in the gas without upstream pressure reduction devices and the associated limitations of such devices, as discussed above.

A preferred embodiment of the present invention has been described above. However, it will be appreciated that variations and modifications may be made to that embodiment within the scope of the appended claims.

What is claimed is:

1. An apparatus for detecting particles in a particle-containing gas at a pressure greater than about 0 psig, comprising:
    a gas distribution line containing a pressurized gas having a pressure greater than about 0 psig; and
    a condensation nucleus counter in fluid communication with the pressurized gas in the gas distribution line, wherein the condensation nucleus counter is adapted to receive a stream of the pressurized gas at a pressure substantially equal to the pressure of the pressurized gas in the gas distribution line.

2. An apparatus as in claim 1, wherein the pressurized gas is selected from the group consisting of $SiCl_4$, $PH_3$, $B_2H_6$, $AsH_3$, $SiF_4$, $Si_2H_6$, $NH_3$, $BCl_3$, $BF_3$, $Cl_2$, $H_2$, HBr, HCl, HF, $NF_3$, $N_2O$, $O_2$, $SiH_4$, $WF_6$, $N_2$, Ar, He, $CF_4$, $CHF_3$, $C_2F_6$, and $SF_6$, and mixtures thereof.

3. An apparatus as in claim 1 further comprising a means for determining the number of at least one particle in the pressurized gas.

4. An apparatus as in claim 3 further comprising a means for tabulating the number of the at least one particle.

5. An apparatus as in claim 4, wherein the means for tabulating is a computer.

6. An apparatus as in claim 1, wherein the condensation nucleus counter comprises:
    (a) a reservoir block;
    (b) an inlet tube adapted to receive the stream of the pressurized gas and to deliver said stream into the reservoir block;
    (c) a saturator disposed inside the reservoir block, wherein the saturator is heated by a heater mounted in thermal contact with the reservoir block;
    (d) a working fluid disposed inside the saturator;
    (e) a sintered metal wick partially submerged in the working fluid;
    (f) a condenser adapted to receive a stream of the pressurized gas from the saturator;
    (g) an aerodynamic focusing nozzle adapted to receive the stream of the pressurized gas stream containing droplets;
    (h) an optical detection chamber having a droplet sensing device to count and identify the droplets in the pressurized gas stream containing droplets; and
    (i) an outlet tube adapted to vent the pressurized gas stream containing droplets from the optical detection chamber.

7. An apparatus as in claim 1, wherein the condensation nucleus counter is constructed of materials resistant to corrosion and to reaction with the pressurized gas selected from the group consisting of $SiCl_4$, $PH_3$, $B_2H_6$, $AsH_3$, $SiF_4$, $Si_2H_6$, $NH_3$, $BCl_3$, $BF_3$, $Cl_2$, $H_2$, HBr, HCl, HF, $NF_3$, $N_2O$, $O_2$, $SiH_4$, $WF_6$, $N_2$, Ar, He, $CF_4$, $CHF_3$, $C_2F_6$, and $SF_6$, and mixtures thereof.

8. A gas distribution system containing a pressurized gas having a pressure greater than about 0 psig, the improvement comprising:
    a condensation nucleus counter in fluid communication with the pressurized gas distribution system, wherein the condensation nucleus counter is adapted to receive a stream of the pressurized gas at a pressure substantially equal to the pressure of the gas in the gas distribution system.

9. A method of detecting particles in a particle-containing gas at a pressure greater than about 0 psig, comprising the steps of:
    providing a gas distribution line containing a pressurized gas at a pressure greater than about 0 psig;
    providing a condensation nucleus counter in fluid communication with the pressurized gas in the gas distribution line, wherein the condensation nucleus counter is adapted to receive a stream of the pressurized gas at a pressure substantially equal to the pressure of the pressurized gas in the gas distribution line; and
    introducing a stream of the pressurized gas into the condensation nucleus counter at a pressure substantially equal to the pressure of the pressurized gas in the gas distribution line.

10. A method as in claim 9, further comprising the step of determining the number of at least one particle in the pressurized gas - introduced into the condensation nucleus counter.

11. A method as in claim 9, wherein the pressurized gas is selected from the group consisting of $SiCl_4$, $PH_3$, $B_2H_6$, $AsH_3$, $SiF_4$, $Si_2H_6$, $NH_3$, $BCl_3$, $BF_3$, $Cl_2$, $H_2$, HBr, HCl, HF, $NF_3$, $N_2O$, $O_2$, $SiH_4$, $WF_6$, $N_2$, Ar, He, $CF_4$, $CHF_3$, $C_2F_6$, and $SF_6$ and mixtures thereof.

12. A method as in claim 10, further comprising the step of tabulating the number of the at least one particle.

13. A method as in claim 12, wherein a computer is used for tabulating.

14. A method as in claim 9, wherein the particles are detected at an at least approximately 50% counting efficiency.

15. A method as in claim 9, wherein the pressure is about 60 psig.

16. A method as in claim 10, wherein the step of determining the number of at least one particle in the pressurized gas comprises the sub-steps of:
    (a) passing a particle-containing gas mixed with a working fluid vapor into a condensation zone;
    (b) condensing the working fluid vapor on at least one particle in the particle-containing gas having a minimum size corresponding to a minimum temperature of a condensing zone to form at least one droplet; and
    (c) detecting the droplets and counting the number of droplets by appropriate sensing and tabulation.

17. A method as in claim 16, wherein the working fluid is perfluorotrimethylcyclohexane.

18. A method as in claim 16, wherein the working fluid is a non-reactive fluid.

19. A method as in claim 18, wherein the non-reactive working fluid is Multifluor® fluid.

* * * * *